US00PP36690P2

(12) United States Plant Patent
Hinkley

(10) Patent No.: US PP36,690 P2
(45) Date of Patent: May 20, 2025

(54) ***COTONEASTER* PLANT NAMED 'MONSHGUS'**

(50) Latin Name: ***Cotoneaster* hybrid**
Varietal Denomination: MONSHGUS

(71) Applicant: Monrovia Nursery Inc, Azusa, CA (US)

(72) Inventor: Daniel J Hinkley, Indianapolis, WA (US)

(73) Assignee: Monrovia Nursery, Azusa, CA (US)

( * ) Notice: Subject to any disclaimer, the term of this patent is extended or adjusted under 35 U.S.C. 154(b) by 0 days.

(21) Appl. No.: 18/743,704

(22) Filed: Jun. 14, 2024

(51) Int. Cl.
*A01H 5/00* (2018.01)
*A01H 6/74* (2018.01)

(52) U.S. Cl.
USPC ..... Plt./226

(58) Field of Classification Search
USPC ..... Plt./226
See application file for complete search history.

(56) References Cited

PUBLICATIONS https://batesnursery.com/products/1-cotoneaster-shear-genius; Retrieved from the Internet on Sep. 26, 2024.*
https://nurseryguide.com/find_plants/c.%20%E2%80%98monshgus%E2%80%99%20ppaf%20(shear%20genius%E2%84%A2cotoneaster) Retrieved from the Internet on Sep. 26, 2024.*
Shear genius.*
Monshgus.*

* cited by examiner

*Primary Examiner* — Susan McCormick Ewoldt

(57) ABSTRACT

A new and distinct variety of *Cotoneaster* plant named 'MONSHGUS' is disclosed, characterized by a very narrow, upright plant form with dense growth. Plants of 'MONSHGUS' have been observed to have a mature size of 5 feet tall and 2 to 3 feet wide. The new variety is suitable for use as a hedge and can be sheared into formal shapes. The foliage is small and dense, creating a fine textured appearance. The new cultivar is a *Cotoneaster*, suitable for horticultural purposes.

2 Drawing Sheets

Latin name of the genus and species: *Cotoneaster* hybrid.
Variety denomination: 'MONSHGUS'.

BACKGROUND OF THE INVENTION

The new cultivar, hereinafter referred to as 'MONSHGUS', was discovered as part of a breeding program at a commercial nursery in Dayton, OR. The intention of the breeding program was to develop new *Cotoneaster* varieties with novel plant habits for commercial ornamental purposes. This new discovery is the result of an open pollination of various unpatented *Cotoneaster* varieties of different species conducted by the inventor during 2019.

'MONSHGUS' was selected as a seedling in June of 2021 at the same commercial nursery in Dayton, Oregon. After identifying the new variety as a potentially interesting selection, the inventor first organized propagation of 'MONSHGUS' by softwood cuttings at the same commercial nursery during the June of 2021. The inventor continued controlled testing and propagation, assessing stability of the unique characteristics of this variety. At least seven generations have been reproduced and have shown that the unique features of this cultivar are stable and reproduced true to type.

SUMMARY OF THE INVENTION

The cultivar 'MONSHGUS' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MONSHGUS' These characteristics in combination distinguish 'MONSHGUS' as a new and distinct *Cotoneaster* cultivar:

1. This is a hedge-type *Cotoneaster* that can be sheared into formal shapes.
2. Plant habit is upright and stays narrow, growing 5' tall and 2-3' wide.
3. Fine textured with small, 0.5-1 cm, circular leaves and dense foliage.

COMPARISON TO PARENT VARIETY

The exact parent varieties cannot be identified.

COMMERCIAL COMPARISON

*Cotoneaster* 'MONSHGUS' can be compared to the commercial variety *Cotoneaster lucidus* unpatented. Plants are similar in most horticultural characteristics; however, plants of the new variety differ in the following:

1. The new variety has 0.5-1 cm, circular leaves that are bright green and glossy; *Cotoneaster lucidus* has dull green elliptic to ovate leaves which are 2.5 cm to 6 cm long and 2.5 cm wide.
2. The new variety has an upright, dense branching habit; *Cotoneaster lucidus* has long, spreading branches.

3. The new variety is fine textured; *Cotoneaster lucidus* is medium textured.
4. Plant size of new variety is 5' tall and 2-3' wide. Plant size of *Cotoneaster lucidus* is 6-10' tall and 6-10' wide.

*Cotoneaster* 'MONSHGUS' can be compared to the unnamed commercial variety *Cotoneaster franchetii* unpatented. Plants are similar in most horticultural characteristics; however, plants of the new variety differ in the following:

1. The new variety has an upright habit with stiff branches; *Cotoneaster franchetii* has sweeping/arching growth.
2. The new variety has 0.5-1 cm, circular leaves that are bright green and glossy; Leaves of *Cotoneaster franchetii* are roughly 2.5 cm long and 1.5 cm wide, elliptic, and pubescent on the undersides.
3. New variety takes well to shearing into formal shapes and keeps tidy appearance; *Cotoneaster franchetii* can tolerate a light prune/shearing before losing its graceful appearance.

BRIEF DESCRIPTION OF THE PHOTOGRAPHS

The accompanying photographs illustrate in full color a typical plant of 'MONSHGUS' grown outdoors in Dayton, OR.

Figure 1:
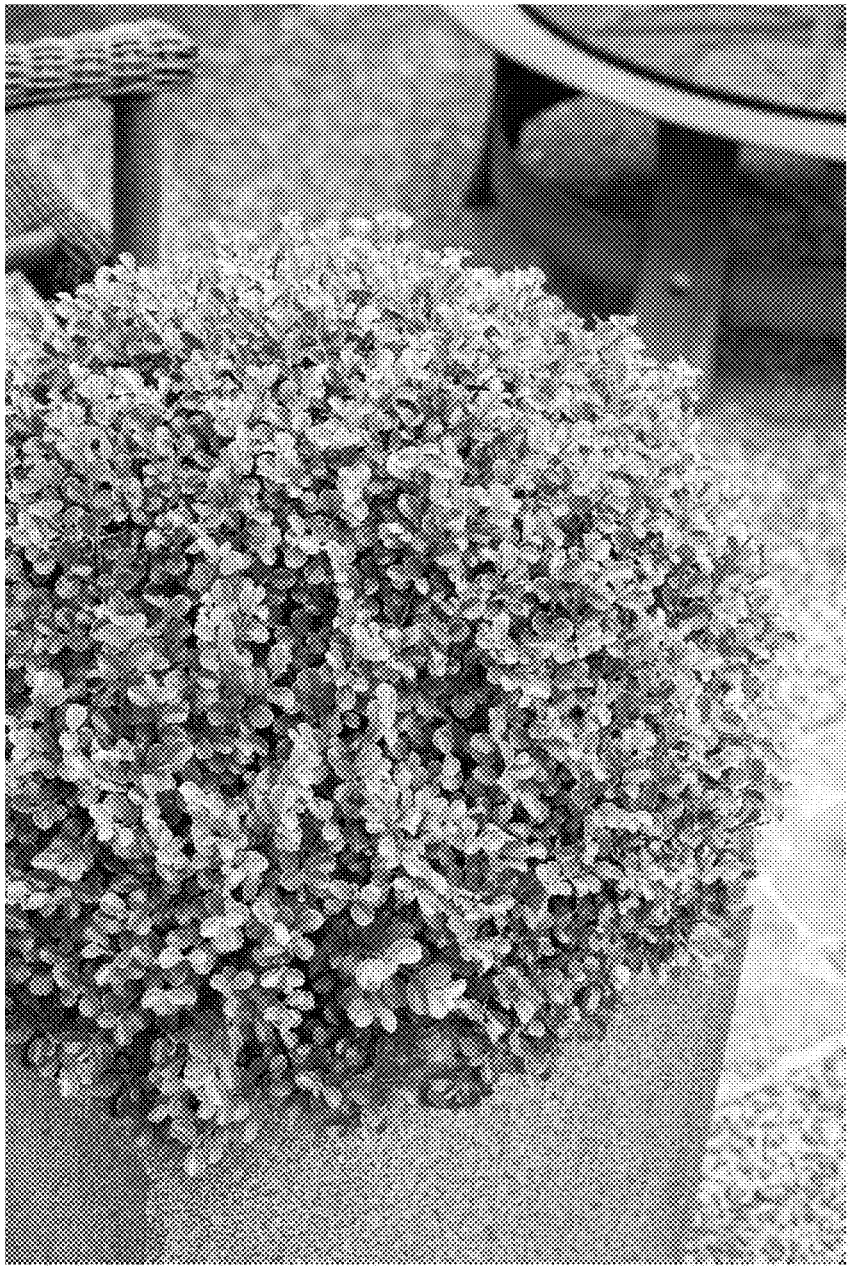
FIG. 1 is a plant of 'MONSHGUS' which has been sheared. The plant is approximately 1.5 years old, in a 2-gallon pot which has been sheared.
Figure 2:
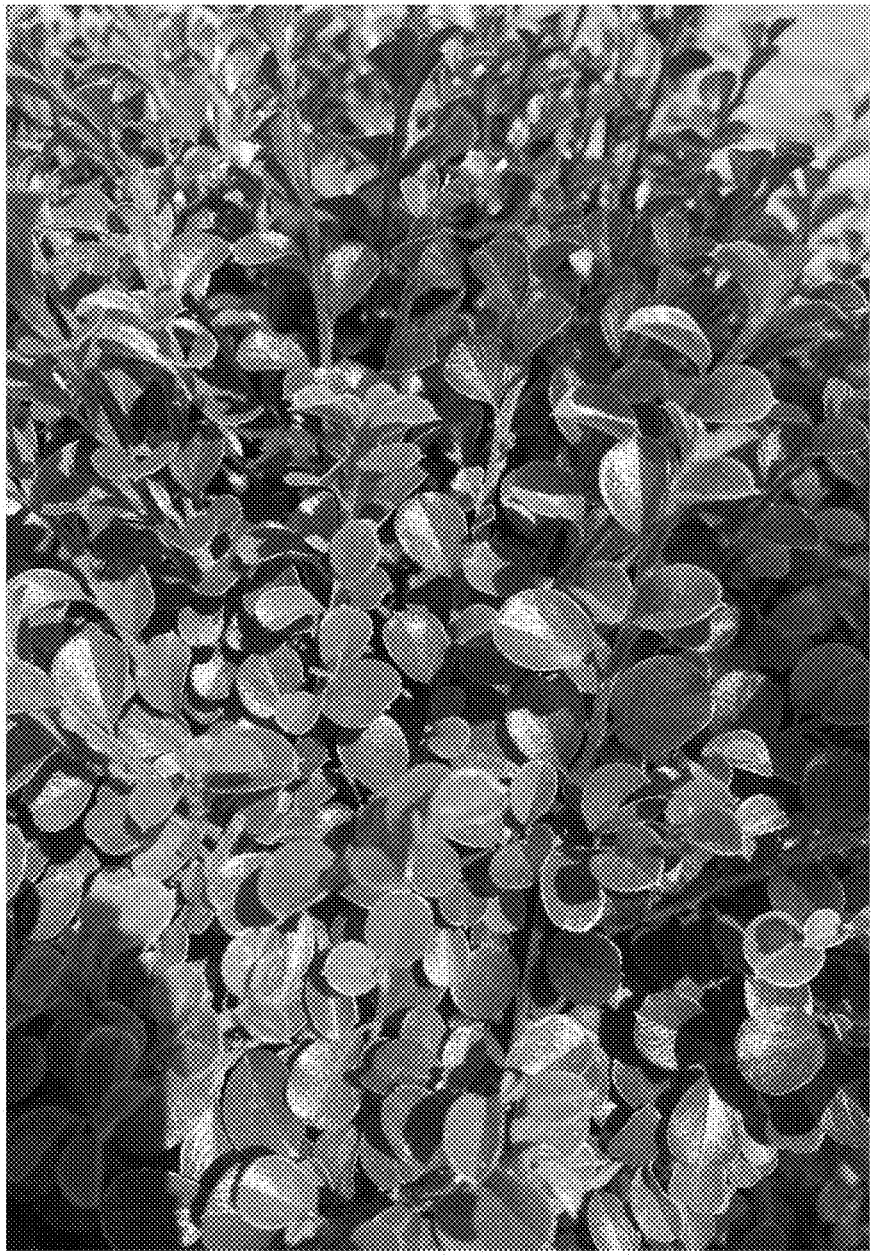
FIG. 2 illustrates the dense foliage. Photos were taken during the Spring and illustrate new growth and young foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MONSHGUS' plants grown outdoors in Dayton, OR. Plants are approximately 1.5 years old, in a 2-gallon nursery container. Measurements and numerical values represent averages of typical plant types.

Botanical classification: *Cotoneaster hybrid* 'MONSHGUS'.

PROPAGATION

Typically by semi-hardwood cuttings in Spring and Summer.

Root description: Semi-woody, moderately dense roots. Colored near RHS Grey-Brown 199A.

PLANT

Growth habit: Upright, narrow V-shape. Semi-evergreen.
Height: Approximately 35 cm.
Plant spread: Approximately 42 cm.
Branching characteristics: Dense and occuring at acute angles. 8 to 12 main branches from pinch.
Length of main branches: Average range 22 cm to 29 cm.
Diameter of main branches: 5 mm.
Lateral branches: Each main branch has an average range of 12 to 18 lateral branches occurring at approximately 25° to 45° from main branch. Alternate.
Diameter of lateral branches: Approximately 3 to 4 mm.
Pinching required:
Details of pinching: Pinch given early at base of plant to encourage dense basal branching.
Branch shape: Round
Branch strength: Strong, resists breakage.
Branch color: Approximately RHS Grey-Brown 199A.
Branch texture: Very slightly scaly.
Lenticels present: No.
Internode length: 8 to 11 mm.

FOLIAGE

Leaf:

*Arrangement*.—Alternate.
*Average length*.—Approximately 5 mm to 10 mm.
*Average width*.—Approximately 5 mm to 8 mm.
*Shape of blade*.—Orbicular
*Apex*.—Retuse.
*Base*.—Tapered.
*Attachment*.—Stalked.
*Margin*.—Entire.
*Texture of top surface*.—Glabrous.
*Texture of bottom surface*.—Glabrous.
*Appearance of top surface*.—Glossy.
*Appearance of bottom surface*.—Matte
*Leaf internode length*.—4 to 5 mm.
*Color*.—Young foliage upper side: Near R.H.S. Green 136A. Young foliage under side: Near R.H.S. Green 138A. Mature foliage upper side: Near R.H.S. Green 136A. Mature foliage under side: Near R.H.S. Green 136C.
*Venation*.—Type: Pinnate. Venation color upper side: Near R.H.S. Yellow-Green 144B. Venation color underside: Near R.H.S. Yellow-Green 144C.

Petiole:

*Average length*.—Approximately 4 mm.
*Diameter*.—Approximately 1 mm.
*Color*.—Near R.H.S. Greyed-Orange 165B.
*Texture*.—Glabrous.

FLOWER

Not observed.

OTHER CHARACTERISTICS

Disease and pest resistance: Neither resistance nor susceptibility to normal diseases and pets of *Cotoneaster* observed.

Temperature tolerance: Observed cold tolerant to USDA Zone 7.

What is claimed is:

1. A new and distinct cultivar of *Cotoneaster* plant named 'MONSHGUS' as herein illustrated and described.

* * * * *